United States Patent [19]

Farrar et al.

[11] Patent Number: 4,959,502
[45] Date of Patent: * Sep. 25, 1990

[54] CATALYSTS AND THEIR USE IN THE HYDROLYSIS OF NITRILES

[75] Inventors: David Farrar; Gerald P. Benn, both of Bradford; Seraj A. M. Karolia, Batley, all of England

[73] Assignee: Allied Colloids Ltd., Great Britain

[ * ] Notice: The portion of the term of this patent subsequent to Mar. 6, 2007 has been disclaimed.

[21] Appl. No.: 275,529

[22] Filed: Nov. 22, 1988

Related U.S. Application Data

[63] Continuation-in-part of Ser. No. 52,030, May 19, 1987, Pat. No. 4,906,776.

[30] Foreign Application Priority Data

Nov. 23, 1987 [GB] United Kingdom ................. 8727379

[51] Int. Cl.$^5$ .................. C07C 231/06; C07C 233/09; B01J 23/84; B01J 25/00
[52] U.S. Cl. .................................... 564/127; 502/301; 502/353; 564/204
[58] Field of Search ........................ 564/127; 502/234; 260/404

[56] References Cited

U.S. PATENT DOCUMENTS

| 3,696,152 | 10/1972 | Haberman et al. | 564/127 |
| 4,056,565 | 11/1977 | Matsuda | 564/127 |
| 4,096,184 | 6/1978 | Nakamura et al. | 564/127 |
| 4,176,137 | 11/1979 | Platz et al. | 502/234 |
| 4,178,310 | 12/1979 | Fetchin et al. | 564/127 |
| 4,593,123 | 6/1986 | Matsuda | 564/127 |

FOREIGN PATENT DOCUMENTS 0875519 5/1953 Fed. Rep. of Germany.
1046586 12/1958 Fed. Rep. of Germany.

OTHER PUBLICATIONS

Khim Tekhnol (Kiev) 1985, 6, pp. 22-23 (translation only).

Primary Examiner—Glennon H. Hollrah
Assistant Examiner—Brian Bemrenick

[57] ABSTRACT

When making an amide by hydrolysis of a nitrile in an aqueous medium containing a Raney copper or other black copper catalyst, the hydrolysis reaction can be improved if the catalyst has been contacted with an aqueous solution of a water soluble vanadium compound followed by thorough rinsing before introduction into the aqueous medium.

12 Claims, No Drawings

CATALYSTS AND THEIR USE IN THE HYDROLYSIS OF NITRILES

This application is a continuation-in-part of our application SN 052,030 now U.S. Pat. No. 4,906,776 filed 19th May 1987, the entire disclosure of which is incorporated by reference and is equivalent to EP-A-246813 (which is discussed below).

It is known to make amides by hydrolysis of the corresponding nitrile in an aqueous medium containing a solid catalyst. The process is of particular value in the manufacture of acrylamide from acrylonitrile.

A wide variety of catalysts have been proposed, including catalysts based primarily on a single metal or metal compound and catalysts based on blends of metals or metal compounds. Examples include the disclosures in GB 1,347,160 and 1,459,685 and U.S. 3,597,481, 3,631,104 and 4,056,565.

The catalysts that have been found most successful in commercial practice, and which are therefore widely discussed in the literature, are the black copper catalysts. Of these, Raney copper has been found to be particularly suitable but others include Ullmann copper and reduced copper catalysts. These reduced copper catalysts may be made by reduction of a solid compound, such as copper oxide, or by precipitation, under reducing conditions, from a solution of a soluble compound such as a copper salt or a soluble complex of copper compound.

There are many proposals in the literature to try to improve the performance of various of these catalysts by the incorporation of other materials in the black copper. Typical examples are in U.S. 3,696,152, GB 1,404,532, 1,417,026 and JP-B-59/18383. Included amongst the numerous additives that have been proposed are vanadium compounds, and such a compound is also exemplified in JP-B-59/18383.

There are also several publications that relate to the production of amides by hydrolysis of nitrile and that specifically recommend that the copper catalyst should contain a vanadium compound. In all of these publications, the black copper catalyst is, in practice, made by precipitation and reduction from a soluble form of copper, and the vanadium compound is incorporated into the black copper catalyst by co-precipitation during the initial formation of the black copper precipitate. Thus in BR 8305831 and EP 145553 an alkaline solution of a divalent copper compound and a complexing agent is formed, a vanadium compound is dissolved into the solution and a reducing agent is added to cause co-precipitation of the black copper catalyst which is then washed. Although it is stated that the amount of vanadium, based on copper, can be in the range 0.5 to 6% on an atomic basis, in many of the examples relatively large amounts of vanadium compound are used.

In JP-B-56/20308 it is stated that a vanadium-containing catalyst can be obtained by reacting metallic copper with a vanadium-containing compound in an aqueous medium. The disclosure includes a long list of suitable forms of copper including various reduced coppers as well as Raney copper, copper powder and Ullmann copper, and alloys with other metals. The disclosure also includes a long list of vanadium compounds that can be used for the process. There are numerous examples but each and every example demonstrates a process in which the catalyst is made by coprecipitation in the presence of a reducing agent. In particular, in most of the examples the coprecipitation is brought about by adding ammonium metavanadate to an aqueous solution of reducing agent and copper compound. There is no suggestion in JP-B-56/20308 how the final catalyst could be made except by coprecipitation.

In Khim Tekhnol (Kiev) 1985, 6, 22-3 and Chemical Abstracts Volume 104 No.130293Z a process is described in which metallic copper, copper salt and vanadium salt are combined to provide an aqueous medium that contains catalyst and that is used for nitrile hydrolysis. It is shown that best results are achieved when the amount of vanadium is in the range 25 to 50% based on copper. It is warned that the operating life of the catalyst is short.

It appears that the described process requires the presence of soluble vanadium in solution in the aqueous medium in which the nitrile is being hydrolysed. Another disclosure of such a process is in GB 1,562,323. The amount of vanadate is preferably from 10% to 1000% based on copper.

It is known from DE-C-1046586 to make an oxidation catalyst by impregnating Raney copper with an aqueous solution of vanadyl sulphate followed by drying of the catalyst. Since the catalyst is to be an oxidation catalyst it is inevitable that the vanadium, and probably also the copper, would be in a highly oxidised form during use, and probably also during the drying step, but this is satisfactory since vanadium pentoxide is known to be a good oxidation catalyst. However it is also known that oxidation of a black copper catalyst will deactivate the catalyst if it is to be used for hydration of a nitrile and so this disclosure is of no relevance to improving the production of amide by hydrolysis of nitrile.

Many of the disclosures in the literature of modifications of copper catalysts for this process are concerned with maximising the conversion of nitrile to amide. Conversion tends to be increased by increasing the temperature of reaction. This is why it is normal in commercial practice to perform the reaction at above 100° C. under pressure, even though some patents suggest that lower temperatures are satisfactory. Unfortunately increased conversion of acrylonitrile is generally accompanied by increased formation of undesirable by-products such as ethylene cyanohydrin.

Increased conversion would be very desirable as it would allow an increased rate of production using the same apparatus and/or energy input and/or catalyst amount, or it would allow an equivalent rate of production using a smaller apparatus and/or lower energy input and/or lower catalyst amount. Reduced by-product formation would be desirable as it would eliminate or reduce the need for purification procedures.

Attainment of these objectives using copper catalyst technology of the same type as is already in use, and in particular Raney copper technology, would be desirable as it would permit maximum utilisation of existing capital equipment and know-how.

It would therefore be desirable to be able to modify a black copper catalyst, especially a Raney copper catalyst, system so as to improve the conversion and/or to reduce the by-product formation and/or to permit good conversion at much lower temperatures than have previously been commercially satisfactory, and in particular under atmospheric pressure. In particular it would be desirable to be able to modify a Raney copper catalyst system so as simultaneously to improve the conversion (or permit a lower reaction temperature) and reduce the by-product formation.

In EP-A-246813 (published 25th November 1987, after the priority date of this application) is described how this objective could be achieved by including vanadium metal, in an amount of 0.01 to 10% by weight, in the black copper metal catalyst.

It is stated in that application that it appeared that the vanadium remained in the metallic form throughout the process. It is stated that the use of compounds of vanadium (naming vanadium oxide and copper vanadate) does not give the advantages of the invention. Example 14 showed that poor results were obtained when the hydrolysis was conducted in the presence of Raney copper and vanadyl nitrate, in contrast to Raney copper and metallic vanadium. Example 15 showed various catalysts made by reduction of a mixture of copper compounds and vanadium compounds were inferior to catalysts based on Raney copper.

Although these statements are all correct, it has been found one particular way of incorporating vanadium into a black copper catalyst that does, despite the poor results discussed above, give useful improvements in activity of the catalyst for the hydrolysis of nitrile to amide.

In the invention is made an amide of the formula $RCONH_2$ where R is a hydrocarbon group of 1 to 10 carbon atoms by hydrolysis of the corresponding nitrile RCN in an aqueous medium containing a copper catalyst containing vanadium, and the process is characterised in that the catalyst has been made by forming a black copper catalyst and then improving the activity of the catalyst by contacting it with an aqueous solution of a water soluble vanadium compound and then rinsing it with water until the catalyst is substantially free of water soluble vanadium compound.

By this technique, it is possible to achieve a very useful increase in the activity of the black copper catalyst, for instance in terms of increased rate of production and/or reduced by-product formation.

Although the mechanism is unclear, it appears that the contact with the vanadium solution causes beneficial modification of the surface properties of the black copper catalyst. Such a catalyst is, in any event, a catalyst for the hydrolysis reaction. This method is in complete contrast to the coprecipitation techniques that have always been used in the prior art and that involve vanadium being trapped within the catalyst.

Another essential feature of the process is that the catalyst should be rinsed free of soluble vanadium compound before it is introduced into the hydrolysis reaction, since the presence of soluble vanadium compounds in the reaction medium is undesirable, as is shown in EP 0246813.

The black copper catalyst must have been preformed. Normally it has, before the treatment step of the invention, activity in the process in the sense that it can promote the hydrolysis of nitrile to amide. It must be black or very dark and can be any of the black coppers described in EP 0246813. Thus it can be a reduced copper catalyst or Ullman copper, but preferably it is Raney copper. The initial manufacture of the black copper catalyst can be by conventional techniques. For instance Raney copper can be made by leaching a copper-aluminium alloy with an alkali, followed by rinsing.

The black copper catalyst that is provided for the process may be a conventional catalyst that is available commercially or may be manufactured on site for use in the process. Generally it has not previously been used, but an advantage of the invention is that a previously used black copper catalyst that has become partially deactivated during use can be reactivated by the treatment with the solution containing vanadium, followed by rinsing. Thus a black copper catalyst can be recovered from the hydrolysis process at a stage when it has tended to become deactivated, reactivated by the treatment with vanadium followed by rinsing, and then re-used.

The preferred vanadium compounds are those in which the vanadium is in the cationic state, and in particular the preferred compounds are vanadyl compounds, such as the sulphate or nitrate, vanadyl sulphate being preferred.

Other soluble vanadium compounds that can be used include compounds in which the vanadium is in the anionic state, namely vanadates. These are generally supplied in the form of ammonium or alkali metal (especially sodium) vanadates.

It is, of course, necessary to select a vanadium compound, and its conditions of application, such that the treatment results in an improvement in the activity of the catalyst and if it is found that any particular vanadium compound does not give a desired improvement then a different compound should be tried. For instance there is some evidence that metavanadates may tend to fail to give an improvement in activity in some application methods (despite their use in the coprecipitation technique of JP-B-56/20308) whereas orthovanadates, especially sodium orthovanadate, do give improvement even in conditions where metavanadate may not. In general, however, the preferred vanadium compound is vanadyl sulphate.

The concentration of the solution that is used to contact the Raney or other black metal catalyst should, calculated as vanadium metal, be at least 5ppm. Generally it is at least 0.01%, usually at least 0.05%. It can be up to 20% but usually it is below 10%. For most purposes amounts in the range 0.1 to 5% are suitable. Generally it is preferred that the concentration should be above 0.2% and often the concentration is not more than 1% or sometimes 2%. All percentages in this specification are by weight unless otherwise specified.

The contact between the solution and the catalyst is preferably achieved by mixing the catalyst, generally in particulate form, with a volume of the solution that is substantially greater than the settled volume of the catalyst. The weight of black copper per millilitre of solution is usually 0.05 to 0.5 grams.

The contact conditions are preferably such that the amount of vanadium (measured as metal) that is deposited on to the black copper is from about 0.01 to about 10% by weight based on the weight of black copper. The amount is usually at least 0.1% but below 5% and often below 2%. It is often preferred that the amount is above 0.2%. Amounts of below 1% are often preferred.

The contact between the solution and the black copper should be at least 1 minute and usually is at least 0.1 hours, normally at least 0.25 hours. Best results are generally obtained when the contact is maintained for at least 0.5, or more usually at least 1 hour.

There is usually no advantage in maintaining the contact for longer than 24 hours or even for longer than 12 hours. Indeed there can be some disadvantage, in some instances, in maintaining the contact for too long, for instance above about 4 hours or, at the most, above about 6 hours, since longer contact appears to result in reduction in performance and possibly even in deactivation of the catalyst. The preferred period of contact is therefore 0.5 or 1 hour up to 4 hours. Around 2 hours is often optimum.

It has been observed that copper is dissolved into the treatment solution during the process.

After performing the contact for the chosen period, the catalyst must then be rinsed with water sufficiently for the catalyst to be substantially free of water soluble vanadium compound, that is to say the rinse solution should be substantially free of dissolved vanadium compound. The reason for this is that significant amounts of soluble vanadium compound in the subsequent hydrolysis aqueous medium interfere with the reaction and so the amount of soluble vanadium compound that can be washed from the catalyst by the hydrolysis aqueous medium must be reduced to such a low amount that it does not significantly interfere with the hydrolysis reaction. This washing also has the effect of rendering the catalyst substantially neutral. Prior to the washing the catalyst will have been acidic (if the contact was with a vanadyl solution) or alkaline (if the contact was with a vanadate solution). The rinsing may be by repeated decantation with water. The water is usually deionised water, at least in the later stages of decantation.

The black copper catalyst must be protected from oxidation or other deactivation conditions before, during and after the activation process and during the hydrolysis process, as is conventional for catalysts of this type for the hydrolysis reaction. Accordingly the activation and hydrolysis processes are normally conducted using deoxygenated solutions under an atmosphere that does not cause oxidation. The black copper catalyst is normally provided initially as a deoxygenated aqueous suspension, and the catalyst should be maintained throughout the activation process and up to its incorporation into the aqueous medium as a deoxygenated aqueous suspension, and the resultant suspension is then introduced into the deoxygenated aqueous medium.

The black copper catalyst is normally particulate, for instance as described in EP 246813.

Despite the need to avoid uncontrolled oxidation of the catalyst prior to introduction into the aqueous hydrolysis medium, the activated catalyst (or the initial black copper oxide catalyst) may be subjected to controlled preoxidation as described in EP 78178.

The hydrolysis medium may be of known content. It must however be substantially free of dissolved vanadium compound. Preferably it consists essentially of water, the nitrile, the amide that is formed, optionally polymerisation inhibitor such as monovalent copper, activator such as copper nitrate or other materials known for this, and optionally reagent that reduces by-product formation, as described in WO86/00614. The starting nitrile, the amide end product and the hydrolysis conditions may be as described in that or, in particular, as described in EP 246813. Thus a preferred process comprises hydrolysis of acrylonitrile to acrylamide using Raney copper that has been activated by contact with vanadyl sulphate or sodium orthovanadate, followed by rinsing, the hydrolysis being conducted in the presence of copper nitrate as accelerator and of copper acetate or acetic acid as agent for reducing by-product formation.

Despite references in the literature to performing the hydrolysis process at temperatures below 100° C., in practice the processes were normally conducted at temperatures above 120° C. In the invention it is particularly preferred to conduct the process at temperatures of not more than 115° C., for instance 100 to 110° C. although lower temperatures, down to 95° C. or even down to 75° C. can be used while still maintaining a useful yield of acrylamide.

The following are some examples. In each of these,
ACM=acrylamide
ECNH=ethylene cyanohydrin ($\beta$-hydroxy propionitrile)

An ACM concentration of 46.6% would represent complete conversion of the acrylonitrile.

The selectivity of the catalyst is defined as $$\frac{\% ECNH \times 100}{\% ACM}$$

and should be as low as possible.

In each example a closed tube test was conducted as described on page 16 of EP 246813 at 90° C.

Example 1

A solution of 0.19% vanadium, as vanadyl (IV) sulphate was made in freshly deoxygenated, deionised water and added to a Raney copper catalyst such that 0.95 g of vanadium was present per gram of Raney copper. The concentration of vanadium in the supernatant liquor was 950 ppm.

Samples of catalyst were removed at regular intervals and washed down before reacting with acrylonitrile and water. The following results were obtained.

| Contact time | ACM % | ECNH % | Selectivity | Adsorbed V |
|---|---|---|---|---|
| Raney copper black | 9.64 | 0.0159 | 0.17 | — |
| 30 mins | 21.88 | 0.0160 | 0.07 | 0.47 |
| 60 mins | 23.08 | 0.0142 | 0.06 | 0.53 |
| 120 mins | 23.93 | 0.0067 | 0.03 | 0.75 |
| 240 mins | 25.51 | 0.0113 | 0.04 | 0.65 |

Example 2

12.5 g Raney copper was washed with 100 g vanadyl sulphate solution (containing 1.72% vanadium). It was allowed to settle and one sample was immediately removed (t=0) and other samples were removed at 1, 2 and 4 hours, and after standing overnight. The results were as follows.

| Contact time | ACM % | ECNH % |
|---|---|---|
| Raney copper | 8.55 | 0.026 |
| t = 1 | 24.34 | 0.019 |
| t = 2 | 25.06 | 0.023 |
| t = 4 | 24.4 | 0.016 |
| Overnight | 11.4 | 0.009 |

Example 3

Varying amounts of a solution of vanadyl (IV) sulphate in deoxygenated, deionised water were added to Raney copper catalyst such that the level of vanadium relative to catalyst was from 38 ppm to 9.5%. After regular agitation over a two hour period the catalysts were isolated and tested as in Example 1. The following results were obtained.

| Concentration of V (based on catalyst) | ACM/% | ECNH/% | Selectivity |
|---|---|---|---|
| 9.5% | 22.90 | 0.0112 | 0.05 |
| 1900 ppm | 17.64 | 0.0186 | 0.10 |
| 380 ppm | 12.08 | 0.0289 | 0.24 |
| 38 ppm | 10.10 | 0.0130 | 0.13 |
| Raney copper-blank | 9.15 | 0.0184 | 0.20 |

Example 4

Raney copper catalyst was mixed with varying amounts of vanadyl sulphate (5, 10 and 19% measured as V based on catalyst) and water and acrylonitrile added. The mixture was reacted at 90° C. for 1 hour. Substantially no acrylamide was formed.

A sample of Raney copper was treated with sulphuric acid to reduce the pH to 3. This is the pH that exists when the Raney copper is treated with a vanadyl sulphate solution to give 19% V based on catalyst. This was also reacted with acrylonitrile and water. The yield was marginally improved (11.93% compared to 9.42%) but the selectivity was worse (0.29 compared to 0.1) relative to the results with the untreated Raney copper catalyst.

This demonstrates that pretreatment merely with acidic sulphate-containing solution is ineffective, and that the presence of dissolved vanadyl cation during the hydrolysis is very undesirable.

Example 5

Sodium orthovanadate ($Na_3VO_4$) and sodium metavanadate ($NaVO_3$) were used to treat a Raney copper catalyst at 5% V on catalyst as a 5000 ppm V solution in water. After a two hour reaction period the catalysts were isolated and rinsed, and then used as the catalyst in the hydrolysis reaction.

As a comparison, hydrolysis was conducted using untreated Raney copper catalysts but with a reaction medium to which 1% $NaVO_3$ and $Na_3VO_4$ respectively had been added. The following results were obtained.

| Raney Copper | ACM/% | ECNH/% | Selectivity |
|---|---|---|---|
| Untreated | 9.27 | 0.0162 | 0.17 |
| 5% V treatment as $NaVO_3$ | 8.89 | 0.0089 | 0.10 |
| 5% V treatment as $Na_3VO_4$ | 17.61 | 0.0186 | 0.11 |
| Untreated plus $NaVO_3$ | 3.20 | 0.0220 | 0.69 |
| Untreated plus $Na_3VO_4$ | 2.16 | 0.3990 | 18 |

These examples demonstrate that it is possible to improve yield of acrylamide whilst maintaining selectivity and/or to improve selectivity whilst maintaining yield as a result of treating the preformed black catalyst with the vanadium compound in the manner defined herein. These results, coupled with the results in examples 14 and 15 of EP 246813, demonstrate the benefits that are obtainable from the invention compared to the coprecipitation techniques of the prior art and the processes in which soluble vanadium compound is included in the aqueous hydrolysis medium.

We claim:

1. A process of making an amide of the formula $RCONH_2$ where R is a hydrocarbon of 1 to 10 carbon atoms by hydrolysis of the corresponding nitrile RCN in an aqueous medium containing a copper catalyst containing vanadium, characterized in that the catalyst has been made by providing a black copper catalyst and then improving its activity by contacting it with an aqueous solution of a water soluble vanadium compound and then rinsing the catalyst with water until the catalyst is substantially free of water soluble vanadium compound.

2. A process according to claim 1 in which the black copper is Raney copper.

3. A process according to claim 2 in which the soluble vanadium compound is a vanadyl compound.

4. A process according to claim 2 in which the soluble vanadium compound is vanadyl sulphate.

5. A process according to claim 2 in which the soluble vanadium compound is a vanadate compound.

6. A process according to claim 2 in which the soluble vanadium compound is an orthovanadate compound.

7. A process according to claim 2 in which the soluble vanadium compound is sodium orthovanadate.

8. A process according to claim 2 in which the solution of soluble vanadium compound contains 0.1 to 2% by weight vanadium.

9. A process according to claim 2 in which the catalyst, after the contact and rinsing, has a vanadium content of 0.1 to 2%.

10. A process according to claim 2 in which the contact is performed for from 1 to 4 hours.

11. A process according to claim 2 in which the nitrile is acrylonitrile and the amide is acrylamide.

12. A process according to claim 1 in which the catalyst has been made by contacting Raney copper with an aqueous solution of vanadyl sulphate and then rinsing with water and in which the hydrolysis is conducted using the preformed catalyst and in the presence of copper nitrate and acetic acid or copper acetate.

* * * * *